(12) United States Patent
Smith et al.

(10) Patent No.: US 10,675,240 B2
(45) Date of Patent: *Jun. 9, 2020

(54) TRANSDERMAL CANNABINOID FORMULATIONS

(71) Applicant: MM Technology Holdings, LLC, Denver, CO (US)

(72) Inventors: Nicole Smith, Centennial, CO (US); Noel Erwin Palmer, Bozeman, MT (US)

(73) Assignee: MM Technology Holdings, LLC, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/044,361

(22) Filed: Jul. 24, 2018

(65) Prior Publication Data

US 2019/0133928 A1   May 9, 2019

Related U.S. Application Data

(63) Continuation of application No. 15/195,751, filed on Jun. 28, 2016, now Pat. No. 10,028,904, which is a continuation-in-part of application No. 14/561,091, filed on Dec. 4, 2014, now Pat. No. 9,375,417.

(51) Int. Cl.
*A61K 9/00* (2006.01)
*A61K 47/24* (2006.01)
*A61K 47/14* (2017.01)
*A61K 31/05* (2006.01)
*A61K 31/01* (2006.01)
*A61K 31/352* (2006.01)

(52) U.S. Cl.
CPC ............ *A61K 9/0014* (2013.01); *A61K 31/01* (2013.01); *A61K 31/05* (2013.01); *A61K 31/352* (2013.01); *A61K 47/14* (2013.01); *A61K 47/24* (2013.01)

(58) Field of Classification Search
CPC .................................................. A61K 9/0014
USPC ....................................................... 514/454
See application file for complete search history.

(56) References Cited

U.S. PATENT DOCUMENTS

| | | | |
|---|---|---|---|
| 3,952,099 A | 4/1976 | Smith | |
| 4,810,499 A | 3/1989 | Nuwayser | |
| 5,540,934 A | 7/1996 | Touitou | |
| 5,607,691 A | 3/1997 | Hale et al. | |
| 5,656,286 A | 8/1997 | Miranda et al. | |
| 5,662,926 A | 9/1997 | Wick et al. | |
| 5,676,969 A | 10/1997 | Wick et al. | |
| 5,679,373 A | 10/1997 | Wick et al. | |
| 5,719,197 A | 2/1998 | Kanios et al. | |
| 6,010,715 A | 1/2000 | Wick et al. | |
| 6,100,259 A | 8/2000 | Xiang et al. | |
| 6,113,940 A | 9/2000 | Brooke et al. | |
| 6,132,762 A | 10/2000 | Cristobal | |
| 6,328,992 B1 | 12/2001 | Brooke et al. | |
| 6,441,014 B2 | 8/2002 | Talley et al. | |
| 6,703,418 B2 | 3/2004 | Plasse | |
| 6,949,582 B1 | 9/2005 | Wallace | |
| 7,069,691 B2 | 7/2006 | Brooke et al. | |
| 8,034,843 B2 | 10/2011 | Whittle et al. | |
| 8,449,908 B2 | 5/2013 | Stinchcomb et al. | |
| 8,603,984 B2 | 12/2013 | Newbound et al. | |
| 8,652,511 B2 | 2/2014 | Cottrell et al. | |
| 8,808,734 B2 | 8/2014 | Winnicki | |
| 9,375,417 B2 | 6/2016 | Smith et al. | |
| 10,028,904 B2 | 7/2018 | Smith et al. | |
| 2001/0029257 A1 | 10/2001 | Murdock et al. | |
| 2003/0229027 A1 | 12/2003 | Eissens et al. | |
| 2008/0160070 A1 | 7/2008 | Crawford | |
| 2009/0017120 A1 | 1/2009 | Trimble et al. | |
| 2009/0247619 A1 | 10/2009 | Stinchcomb et al. | |
| 2011/0052694 A1 | 3/2011 | Stinchcomb et al. | |
| 2013/0187126 A1 | 7/2013 | Be Vier et al. | |
| 2013/0281523 A1 | 10/2013 | Letendre et al. | |
| 2014/0200200 A1 | 7/2014 | Piazza et al. | |
| 2014/0271940 A1 | 9/2014 | Wurzer | |
| 2014/0302148 A1 | 10/2014 | Winnicki | |
| 2015/0126595 A1 | 5/2015 | Smith | |
| 2016/0022627 A2 | 1/2016 | Smith | |

FOREIGN PATENT DOCUMENTS

| | | |
|---|---|---|
| EP | 0563507 | 10/1993 |
| WO | WO 2008/024408 | 2/2008 |
| WO | WO 2013/112915 | 8/2013 |

(Continued)

OTHER PUBLICATIONS

Susan Barclay-Nichols, Point of Interest, Sep. 13, 2010, pp. 1.*
Submitted in parent U.S. Appl. No. 15/195,751.*
International Search Report and Written Opinion for PCT/US15/26317, dated Jul. 8, 2015, 14 pp.
Bonam (2013) "Preparation and Evaluation of Pluronic Lecithin Organogel Containing Ricinoleic Acid for Transdermal Drug Delivery", The University of Toledo Digital Repository, Theses and Dissertations, Paper 32, 118 pp.
Dow Corning (2001) "Silicones for Transdermal Drug Delivery Systems" [Brochure] n.d. U.S.A. Dow Corning Corporation.
Egelko (2014) "Court Upholds Crackdown on Pot Dispensaries" found at http://blog.sfgate.com/crime/2014/01/15/court-upholds-crackdown-on-pot-dispensaries/ on May 13, 2014.

(Continued)

*Primary Examiner* — Taofiq A Solola
(74) *Attorney, Agent, or Firm* — Leydig, Voit & Mayer, Ltd.

(57) ABSTRACT

The present invention includes a transdermal composition which contains a pharmaceutically effective amount of a cannabinoid for delivery of the cannabinoid to the bloodstream of a user. The composition may comprise the following components: a surfactant-lecithin organogel; and a cannabinoid. The composition may also comprise an exogenous terpene. The cannabinoid is capable of diffusing from the composition into the bloodstream of the user, and may be used in methods for treating a patient suffering from a condition such as pain, nausea and emesis, convulsions, muscle spasm, inflammation, depression, and cachexia.

20 Claims, 1 Drawing Sheet

(56) References Cited

FOREIGN PATENT DOCUMENTS

| WO | WO 2015/161165 | 10/2015 |
|---|---|---|
| WO | WO 2016/090287 | 6/2016 |

OTHER PUBLICATIONS

Glazer et al. (Feb. 19, 2013) "Things to Keep in Mind When Marking Your Pot" downloaded at http://www.law360.com/articles/4I5339/things-to-keep-in-mind-when-marking-your-pot on Apr. 15, 2014.
Grotenhermen (2003) "Pharmacokinetics and Pharmacodynamics of Cannabinoids" Clin. Pharmacokinet 42(4):327-360.
Lubrizol Technical Data Sheet (2007) "Introducing Pemulen®* Polymeric Emulsifiers", www.pharma.lubrizol.com, Edition: Oct. 15, 2007; Previous Edition: Jan. 2002.
Margetts et al., "Transdermal Drug Delivery: Principles and Opioid Therapy", Continuing Education in Anaesthesia, Critical Care & Pain 7(5):171-176.
Mechoulam et al. (2001) "The Cannabinoids: An overview. Therapeutic implications in Vomiting and Nausea after Cancer Chemotherapy, in Appetite Promotion, in Multiple Sclerosis and in Neuroprotection" Pain Res Manage 2001, 6(2):67-73.
Murdan (2005) "A Review of Pluronic Lecithin Organogel as a Topical and Transdermal Drug Delivery System", Hospital Pharmacist 12:267-270.
N'Da, (2014) "Prodrug Strategies for Enhancing the Percutaneous Absorption of Drugs", Molecules 19:20780-20807.
Polikandritou et al. (1985) Enhancement of the Sensitivity of the Buehler Method by Use of the Hill Top Chamber, J. Soc. Cosmet. Chem. 36:159-168.
Quisno et al. (1983) "A New Occlusive Patch Test System with a Plastic Chamber", J. Soc. Cosmet. Chem. 34:13-19.
Saghir et al., (2010) "Dermal penetration of Ethylene Glycol through Human Skin in vitro", Int. J. Toxicol. vol. 29(3). Abstract, 2 pages. Retrieved online Mar. 18, 2016 at http://www.ncbi.nlm.nih.gov/pubmed/20448259.
Sallan et al. (1980) "Is THC an Effective Antiemetic for Cancer Patients? Opinion 2" CA—A Cancer Journal for Clinicians 30(5): 282-284.
Smith (2014) "Topical Cannabis Preparations: Snake Oil or Healing Options?" downloaded at http://www.compassioncenter.net/topical-cannabis-preparations on Jul. 20, 2014.
Tiwary et al. (2007) "Innovations in Transdermal Drug Delivery: Formulations and Techniques", Recent Patents on Drug Delivery & Formulation 2007, 1(1):23-36.
Touitou et al. (1987) "Transdermal Delivery of Tetrahydrocannabinol" Intl J. of Pharmaceutics 43: 9-15.
Touitou et al. (1988) "Altered Skin Permeation of a Highly Lipophilic Molecule: Tetrahydrocannabinol" Intl J. of Pharmaceutics 43: 17-22.
Willimann et al. (1992) "Lecithin Organogel as Matrix for Transdermal Transport of Drugs", J. of Pharmaceutical Sciences 81(9):871-874.
Israeli Office Action with English translation, dated Dec. 8, 2019, in Israeli Patent Application No. 252550, 7 pp.
U.S. Appl. No. 14/561,091, filed Dec. 4, 2014.
U.S. Appl. No. 15/195,751, filed Jun. 28, 2016.

* cited by examiner

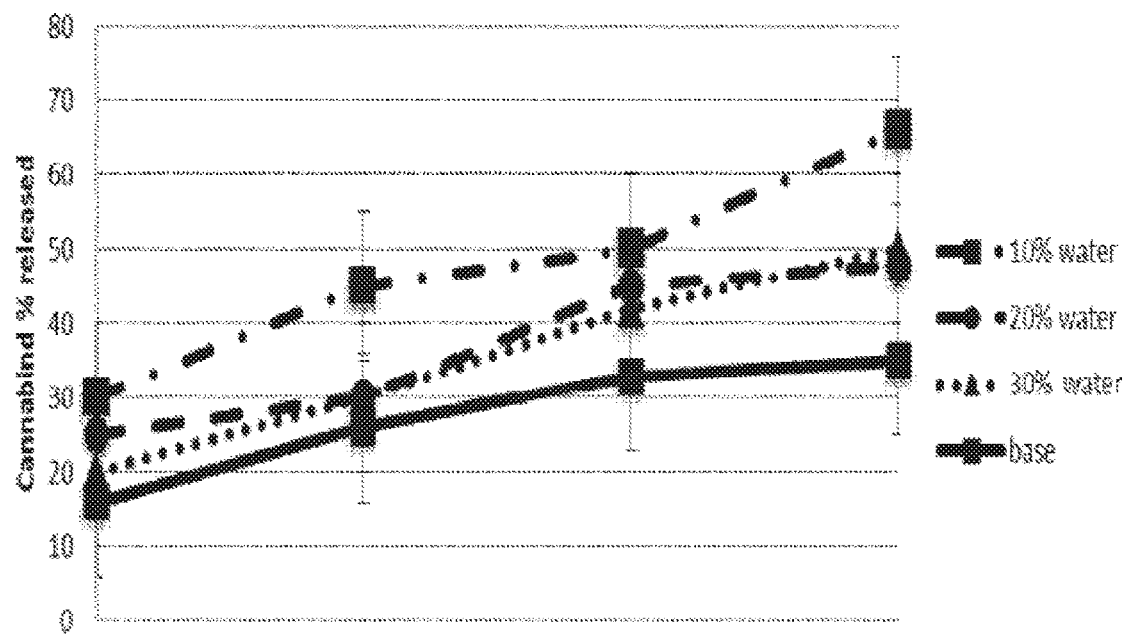

TRANSDERMAL CANNABINOID FORMULATIONS

CROSS-REFERENCE TO RELATED APPLICATIONS

This application is a continuation of and claims priority to pending U.S. application Ser. No. 15/195,751, entitled "Transdermal Cannabinoid Formulations," filed Jun. 28, 2016, which in turn is a continuation in part of U.S. Ser. No. 14/561,091 entitled "Transdermal Cannabinoid Formulations", filed Dec. 4, 2014, now U.S. Pat. No. 9,375,417, issued Jun. 28, 2016, the disclosure of which is hereby incorporated by reference herein in its entirety.

BACKGROUND

The clinical usefulness of the cannabinoids, including $11^9$-tetrahydrocannabinol (/$1^9$-THC), to provide analgesia, help alleviate nausea and emesis, as well as stimulate appetite has been well-recognized. Cannabinoids offer a variety of pharmacological benefits, including, but not limited to, anti-spasmodic, anti-inflammatory, anti-convulsant, anti-psychotic, anti-oxidant, neuroprotective, anti-inflammatory, anti-cancer, and immunomodulatory effects.

Given the therapeutic benefit, it would be advantageous to develop a composition in which cannabinoids are delivered systemically to achieve a therapeutically effective dose. The cannabinoids undergo substantial first-pass metabolism when absorbed from the human gut after oral administration, which suggests alternate forms of dosage. It protects against the influx of toxins and the efflux of water and is largely impermeable to the penetration of foreign molecules, although small, lipophilic molecules can diffuse across the skin.

However, due to the protective function of the skin of a mammal, such as a human, even lipophilic and low molecular weight compounds generally only transfer in small amounts across the skin, resulting in difficulty in achieving therapeutic levels of drug in the bloodstream. Therefore, the success of transdermally administering therapeutically effective quantities of cannabinoids to a mammal in need of such treatment within a reasonable time frame and over a suitable surface area has been substantially limited.

The present invention is directed toward overcoming one or more of the problems discussed above.

SUMMARY OF THE EMBODIMENTS

In one embodiment, the present invention includes a transdermal composition which contains a pharmaceutically effective amount of a cannabinoid for delivery of the cannabinoid to the bloodstream of a user. The composition may comprise the following components: a pharmaceutically effective amount of a cannabinoid, and a surfactant-lecithin organogel which optionally includes acrylic cross-polymer-lecithin. The cannabinoid is capable of diffusing from the composition into the bloodstream of the user.

In some embodiments, a permeation enhancer, which includes isopropyl myristate, is included. In some embodiments, a terpene/terpenoid is included in the composition, which may be myrcene ormenthol.

The compositions of the invention may comprise one or more cannabinoids. In some embodiments, the cannabinoid is a cannabinol, such as THC or CBN. In some embodiments, the cannabinoid is a cannabidiol, such as CBD. In some embodiments, the cannabinoid occurs as a cannabinoid acid comprising a carboxylic acid substituent attached to an aromatic ring such as THCa or CBDa. In some embodiments, the cannabinoid is HTCv or CBC. Mixtures of two or more cannabinoids may also be used; for example, CBD and THC may be used in a 1:1 ratio.

Finally, the instant invention includes methods for treating a patient suffering from a condition such as pain, nausea and emesis, convulsions, muscle spasm, inflammation, depression, and cachexia comprising administering a composition of the instant invention.

Various modifications and additions can be made to the embodiments discussed without departing from the scope of the invention. For example, while the embodiments described above refer to particular features, the scope of this invention also included embodiments having different combination of features and embodiments that do not include all of the above described features.

BRIEF DESCRIPTION OF THE FIGURES

FIG. 1 shows a Franz diffusion cell permeation experiment with different proportions of water in the transdermal formulation.

DETAILED DESCRIPTION

In one embodiment, the present invention includes a transdermal composition which comprises a pharmaceutically effective amount of a cannabinoid for delivery of the cannabinoid to the bloodstream of a user. The composition may comprise a surfactant-lecithin organogel, and at least one cannabinoid. After application to the skin, the cannabinoid is capable of diffusing from the composition into the bloodstream of the user in a therapeutically effective amount. The instant invention is related to applications U.S. 61/981,640 and U.S. 62/087,390, which are incorporated herein by reference in their entirety.

Transdermal drug delivery offers an advantageous mode of drug administration by eliminating first pass hepatic metabolism and providing sustained drug release for a prolonged period of time. It is painless when compared to needles and therefore offers superior patient compatibility. The skin permits the influx of a variety of small molecules that are fairly lipophilic (log P>1.5) and have molecular weight less than 500 Da; cannabinoids generally fulfill these requirements. Also, avoidance of first pass metabolism may prevent or reduce the presence of metabolites.

In some examples, the compositions comprise a surfactant-lecithin organogel, in some embodiments also called a "PLO gel" or "PLO". In some embodiments, the PLO gel is a PLURONIC or a CARBOPOL lecithin organogel. PLO gels is a descriptive term for dermal penetration enhancers which are biphasic compositions comprising a water phase and a lipid phase. In place of PLURONIC the PLO gel may contain other emulsifiers/stabilizers, and so therefore the term "PLO gel" may also be used for compositions lacking PLURONIC, such as those containing CARBOPOL (e.g., acrylate crosspolymers). In some examples, the lipid phase is prepared by mixing isopropyl palmitate (or, alternatively, PPG-2 myristyl ether propionate) and lecithin, and the water phase is prepared by optionally mixing a surfactant such as PLURONIC (a group of surfactants comprising block copolymers based on ethylene oxide and propylene oxide that can function as antifoaming agents) or alternatives such as CARBOPOL and/or PEMULEN with water. Optionally, the water phase may omit surfactants. The water phase and the lipid phase are then added together through high agitation to create one standing compound. A cannabinoid or cannabinoids can be directly added to the compound at this point or can be added during the preparation of the organic phase.

In use of cannabis formulated with PLO according to the present invention, it was surprisingly observed that transdermal delivery was significantly increased over the prior art compositions.

Surfactant-lecithin organogels are non-irritating to the skin and are absorbed quickly. In some embodiments, surfactant-lecithin organogel may include ingredients such as isopropyl palmitate (or PPG-2 myristyl ether propionate), soy lecithin, water, and optionally, PLURONIC F127 or another surfactant such as CARBOPOL. See, e.g., U.S. Patent Publication 2009/0017120 "Phase Stable Lecithin Organogel Composition", which is incorporated herein by reference in its entirety. Alternatively, surfactant-lecithin organogels may be formed with lecithin, a fatty surfactant such as PPG-2 myristyl ether propionate and/or isopropyl myristate, as well as other permeation enhancers, stabilizers, carriers, preservatives, and the like.

about 0.6%, about 0.8%, about 1%, about 1.2%, about 1.4%, about 1.6%, about 1.8%, about 2%, about 2.2%, about 2.5%, about 3%, about 3.5%, about 4%, about 4.5%, or about 5%.

Lecithin is a naturally occurring mixture of diglycerides of fatty acids linked to the choline ester of phosphoric acid. It is used as a penetration enhancer in compounding the PLO gel. It is a liquid at room temperature and may become solid upon cooling. It is normally stored at room temperature. Lecithins vary greatly in their physical form from semiliquids to powders. They are almost odorless and vary from brown to light yellow. They decompose at extreme pH's and are hygroscopic. They will oxidize and darken at high temperatures. Lecithin is usually stored at room temperature and protected from light. Refrigeration may cause the material to separate. Lecithins may be obtained from animal sources, soybeans, egg, dairy, marine sources, rapeseed, cottonseed, sunflower, for example. In some embodiments, the lecithins used in the present invention are from vegetarian sources. The major components of commercial soybean-derived lecithin are: 33-35% soybean oil, 20-21% inositol

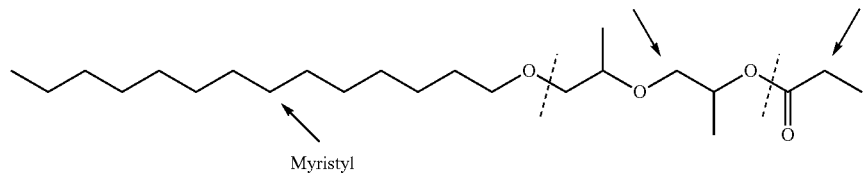 [SMILES: CCCCCCCCCCCCCCOCC(C)OCC(C)OC(=O)CC]

Myristyl

30

The compositions of the invention may include a fatty surfactant such as a propylene glycol ester of fatty acids, for example, PPG-2 myristyl ether propionate, which is a combination of glycols with fatty acids and alcohols and is used as an emollient with a high capacity for spreading.

Propylene glycol esters of fatty acids are mixtures of propylene glycol mono- and diesters of saturated and unsaturated fatty acids derived from edible oils and fats. The products are produced either by direct esterification of propylene glycol with fatty acids or by transesterification of propylene glycol with oils or fats. When prepared by transesterification, the product may contain residual mono- and diglycerides and glycerol. The process may be followed by molecular distillation to separate the monoesters. For example, PPG-2 myristyl ether propionate is a mixture of polypropylene ether glycols with myristate fatty acids. Other combinations of glycols and fatty acids may also be used, for example, propylene glycol oleate, propylene glycol isostearate, propylene glycol laurate, and others as known in the art.

The amount of glycol/fatty acid compound (fatty surfactant) to use includes amounts between about 0.2% and about 5%. Glycol/fatty acid compound (fatty surfactant) may be used in a range of between about 0.2% to 5% wt/wt in the final composition. In one embodiment, glycol/fatty acid compound (fatty surfactant) is used in an amount of about 2%. The amount of glycol/fatty acid compound (fatty surfactant) to use may be between about 0.2% and about 5% of the composition, (w/w) between about 0.4% and about 4.5%, between about 0.6% and about 4%, between about 0.8% and about 3.5%, between about 1% and about 3%, between about 1.2% and about 3.8%, between about 1.4% and about 3.5%, between about 1.6% and about 3%, between about 1.2% and about 2.5% or between about 1.5% and 2.5%. Alternatively, the glycol/fatty acid compound (fatty surfactant) amount can be about 0.2%, about 0.4%, phosphatides, 19-21% phosphatidylcholine, 8-20% phosphatidylethanolamine, 5-11% other phosphatides, 5% free carbohydrates, 2-5% sterols, and 1% moisture. Lecithin may be used in a range of between about 0.5% to 25% wt/wt in the final composition. In one embodiment, lecithin is used in an amount of about 15%. The amount of lecithin to use may be between about 2% and about 24% of the composition, (w/w) between about 4% and about 22%, between about 6% and about 20%, between about 8% and about 18%, between about 10% and about 17%, between about 12% and about 16%, or between about 14% and 15%. Alternatively, the lecithin amount can be about 2%, about 4%, about 5%, about 6%, about 7%, about 8%, about 9%, about 10%, about 11%, about 12%, about 13%, about 14%, about 15%, about 16%, about 18%, about 20%, about 22%, or about 25%.

Suitable surfactants include a number of compounds. Poloxamers, also known by the trade name PLURONIC, are nonionic triblock copolymers composed of a central hydrophobic chain of polyoxypropylene (poly(propylene oxide)) flanked by two hydrophilic chains of polyoxyethylene (poly(ethylene oxide)). Because the lengths of the polymer blocks can be customized, many different poloxamers exist. PLURONIC is a reverse thermal gel and its viscosity increases with higher temperatures.

In one embodiment, the PLURONIC is PLURONIC F127 (F refers to the flake, or solid form; the first two digits refer to the molecular weight multiplied by 300, i.e., 3600 g/mol, and the third digit refers to the percent polyoxyethylate multipled by 10, i.e., 70%). PLURONIC F127 is a long chain polymer that has the unique property of being a solid at room temperature. It is a liquid when at refrigerated temperatures and becomes more viscous upon warming. It is normally stored at around 4° C. Other PLURONIC copolymers may also be used.

Alternatively, PEMULEN brand polymeric emulsifiers (Lubrizol) can be used in place of PLURONIC. PEMULEN polymeric emulsifiers are predominantly high molecular weight polyacrylic acid polymers. Generally, they can be described as copolymers of acrylic or methacrylic acid and a long chain alkyl acrylate cross linked with an allyl ether pentaerythritol or sucrose. These are oil in water emulsifiers which anchor at the oil-water interface and do not build liquid crystalline structures to provide emulsion stability.

The PLO gel can also comprise CARBOPOL polymers (Lubrizol). CARBOPOL polymers are high molecular weight homo- and copolymers of acrylic acid crosslinked with a polyalkenyl polyether.

Another surfactant to use may include polysorbate such as those obtained from polyethoxylated sorbitan and a fatty acid. The polysorbate to use includes fatty acid polysorbates such as Polysorbate 80 (oleic acid). When used, the surfactant may be used in an amount between about 0.5% and 3%, between about 1% and about 2.5%, or about 2%.

The surfactant, for example CARBOPOL, may be used in a range of between about 0.5% to 25% wt/wt in the final composition. In one embodiment, surfactant is used in an amount of about 2%. The amount of surfactant to use may be between about 0.5% and about 24% of the composition, (w/w) between about 0.6% and about 22%, between about 0.8% and about 20%, between about 1% and about 18%, between about 1.2% and about 17%, between about 1.4% and about 16%, or between about 1.6% and 15%. Alternatively, the surfactant amount can be about 0.5%, about 0.6%, about 0.8%, about 1%, about 1.2%, about 1.4%, about 1.6%, about 1.8%, about 2%, about 2.2%, about 2.4%, about 2.6%, about 2.8%, about 3%, about 4%, about 5%, about 10%, or about 15%.

Typically, the oil phase is present at about 22% v/v in a PLO (as lecithin dissolved in isopropyl palmitate in a 1:1 ratio) and an aqueous solution of about 20-30% surfactant such as PLURONIC F127 or PEMULEN/CARBOPOL.

Preparation of PLO base. A PLO base is composed of PLURONIC (or other surfactant, such as PPG-2 myristyl ether propionate) gel and lecithin. A gel is a two-phase colloidal system containing a solid and a liquid phase.

The oil phase may be prepared by mixing lecithin, PPG-2 myristyl ether propionate, and/or other materials such as isopropyl myristate and/or isopropyl palmitate and allowing the mixture to stand overnight to ensure complete dissolution. The role of organic solvent in providing the desired solvent action onto the lecithin molecules is much emphasized. A large variety of organic solvents are able to form gel in the presence of lecithin. Isopropyl palmitate is of particular interest for topical applications of lecithin organogels. This has been attributed to its skin penetration enhancing property as well as its biocompatible and biodegradable nature.

The aqueous phase may be prepared by adding PLURONIC F127 or other surfactant to ice cold water (or room temperature water) and agitating periodically to ensure complete dissolution. PLURONIC or other surfactant gels may be formed by hydrogen bonding by attraction of the surfactant ether oxygen atoms with water protons in aqueous PLURONIC or other surfactant systems. Alternatively the aqueous phase may omit a surfactant. The amount of water to use is in the range of about 1% to about 30% (w/w); between about 2% and about 25%, between about 4% and about 20%, between about 5% and about 18%, between about 6% and about 16%, between about 7% and about 14%, between about 8% and about 12%, or about 10%. Alternatively, the water amount can be about 1%, about 2%, about 3%, about 4%, about 5%, about 6%, about 7%, about 8%, about 10%, about 11%, about 12%, about 14%, about 16%, about 18%, about 20%, or about 30%.

Generally speaking, dispersion of a lipophilic drug in the oil phase may be conducted by mixing the drug with alcohol or propylene glycol. Lipophilic drugs have an uptake capacity of about 5% to about 10% in PLO, generally speaking.

PLO gels are available from a number of suppliers. In a preferred embodiment, PLO gel is obtained from Apothecares (Decatur, Ala.), and includes water, PPG-2 myristyl ether propionate, soy lecithin, ethyl alcohol, PEMULEN TRI, aminomethyl propanol, potassium sorbate, methylparaben, CARBOPOL 2020, propylparaben, and bronopol.

The amount of PLO to use in the present invention is generally between about 20% and about 99.9% of the composition, between about 25% and about 99%, between about 30% and about 98.5%, between about 40% and about 98%, between about 50% and about 97.5%, between about 60% and about 97%, between about 70% and about 96.5%, between about 75% and about 96%, between about 75% and about 95%. Alternatively, the PLO amount can be about 20%, about 30%, about 40%, about 50%, about 60%, about 70%, about 75%, about 80%, about 82%, about 84%, about 86%, about 87%, about 88%, about 89%, about 90%, about 92%, about 94%, about 96%, about 97%, about 97.5%, about 98%, about 98.5%, about 99%, about 99.5, or about 99.9% or more. In some embodiments, the amount to use is about 98%.

All percentages and amounts in the present application, if not otherwise defined, are to be defined as weight percents (w/w).

In some embodiments of the present invention, PLO may be used together with one or more additional penetration enhancers. Additional penetration enhancers may comprise, for example, $C_8$-$C_{22}$ fatty acids. Such fatty acids can comprise oleic acid, undecanoic acid, valeric acid, heptanoic acid, pelargonic acid, capric acid, lauric acid, and eicosapentaenoic acid. In one embodiment, the carrier agent is oleic acid. In another embodiment, carrier agents can include $C_8$-$C_{22}$ fatty alcohols such as, for example, octanol, nonanol, oleyl alcohol, decyl alcohol and lauryl alcohol. In another embodiment, carrier agents can comprise lower alkyl esters of $C_8$-C22 fatty acids such as, for example, ethyl oleate, isopropyl myristate, butyl stearate, and methyl laurate. Carrier agents may also comprise di(lower)alkyl esters of C6-C22 diacids such as diisopropyl adipate; monoglycerides of $C_8$-$C_{22}$ fatty acids such as glyceryl monolaurate; tetrahydrofurfuryl alcohol polyethylene glycol ether; polyethylene glycol, propylene glycol; 2-(2-ethoxyethoxy)ethanol; diethylene glycol monomethyl ether; alkylaryl ethers of polyethylene oxide; polyethylene oxide monomethyl ethers; polyethylene oxide dimethyl ethers; glycerol; ethyl acetate; acetoacetic ester; N-alkylpyrrolidone. In one embodiment, the carrier is isopropyl myristate.

The penetration enhancer can be included in the composition is generally between about 1% and about 40% of the composition, between about 5% and about 38%, between about 10% and about 35%, between about 15% and about 32%, between about 18% and about 30%, between about 20% and about 30%, between about 25% and about 30%, or about 20-about 30%, or about 22 to about 28%. Alternatively, the penetration enhancer amount can be about 2%, about 4%, about 6%, about 8%, about 10%, about 12%, about 14%, about 16%, about 18%, about 20%, about 22%, about 24%, about 26%, about 28%, about 30%, about 32%, about 34%, about 36%, or about 38%, or about 40%. Where the composition comprises oleic acid, the permeation enhancer may be between about 1% and 20%, and in one embodiment, is about 13%. Where the composition comprises isopropyl myristate, the amount may be between about 1% and about 40%, between about 25-35%, and is optionally about 32%. The weight percent used in the composition will also be dependent upon the weight percent of the desired cannabinoid in the cannabis preparation and will be adjusted so that the ratio of the penetration enhancer to amount of desired cannabinoid is constant.

The compositions of the invention may also include stabilizers and carriers as known in the art. For example, carriers and stabilizers may additionally include ingredients such as alcohol, such as ethyl alcohol, in amounts between about 1% and 15%, for example 5%; buffering agents such as aminomethyl propanol, in amounts between about 0.2% and about 15%, or optionally about 2%; humectants such as glycerin, in amounts between about 1% and 10%, for example, about 5%.

Optionally, the compositions of the invention also include preservatives, such as, for example, methyl paraben (between about 0.1% and 1.5%, or about 1%), propyl paraben (between about 0.1% and 1.5%, or about 1%), bronopol (between about 0.1% and 2%, or about 1%), potassium sorbate (between about 0.1% and 2%, or about 1%), and/or tocopherol (between about 1% and 5%, or about 1%), or other known antifungal agents and antioxidants. The compositions of the invention also optionally comprise a carrier compound which can include a terpene and/or terpenoid. Terpenes are a diverse group of organic hydrocarbons derived from 5-carbon isoprene units and are produced by a wide variety of plants. Terpenoids are terpenes which have been chemically modified to add functional groups including heteroatoms. Terpenes/terpenoids are important building blocks for hormones, vitamins, pigments, steroids, resins, and essential oils. Terpenes are naturally present in cannabis; however, they can be removed during the extraction process. Therefore in one embodiment one or more terpenes and/or terpenoids are added to the composition. Terpenes/terpenoids have various pharmaceutical (pharmacodynamic) effects and can be selected for the desired pharmaceutical activities. One or more terpenes/terpenoids can be used in the compositions. In some embodiments, the effects of the cannabinoids are synergized by addition of particular terpenes/terpenoids.

In one embodiment, the terpene/terpenoid includes limonene. Limonene is a colorless liquid hydrocarbon classified as a cyclic terpene. The more common D-isomer possesses a strong smell of oranges and a bitter taste. It is used in chemical synthesis as a precursor to carvone and as a solvent in cleaning products. Limonene is a chiral molecule. Biological sources produce one enantiomer—the principal industrial source—citrus fruit, contains D-limonene ((+)-limonene), which is the (R)-enantiomer (CAS number 5989-27-5, EINECS number 227-813-5). Racemic limonene is known as dipentene. Its IUPAC name is 1-methyl-4-(1-methylethenyl)-cyclohexene. It is also known as 4-isopropenyl-1-methylcyclohexenep-Menth-1,8-dieneRacemic: DL-limonene; dipentene.

Limonene has a history of use in medicine, food and perfume. It has very low toxicity, and humans are rarely allergic to it. Limonene is used as a treatment for gastric reflux and as an anti-fungal agent. Its ability to permeate proteins makes it a useful treatment for toenail fungus. Limonene is also used for treating depression and anxiety. It is reported to assist in the absorption of other terpenoids and chemicals through the skin, mucous membranes and digestive tract. It has immunostimulant properties. It is also used as botanical insecticide The principle metabolites of limonene are (+)- and (−)-trans-carveol, aproduct of 6-hydroxylation) and (+)- and (−)-perillyl alcohol, a product of 7-hydroxylation by CYP2C9 and CYP2C19 cytochromes in human liver microsomes. The enantiomers of perillyl alcohol have been researched for possible pharmacological possibilities as dietary chemotherapeutic agents. They are considered novel therapeutic options in some CNS neoplasms and other solid tumors, especially for treatment of gliomas. The cytotoxic activities of perillyl alcohol and limonene metabolites are likely due to their antiangiogenic properties, hyperthermia inducing effects, negative apoptosis regulation and effect on Ras pathways.

In another embodiment, the terpene/terpenoid includes linalool. Linalool is a naturally occurring terpene alcohol chemical found in many flowers and spice plants with many commercial applications, the majority of which are based on its pleasant scent (floral and slightly spicy). It is also known as β-linalool, linalyl alcohol, linaloyl oxide, p-linalool, allo-ocimenol, and 3,7-dimethyl-1,6-octadien-3-ol. Its IUPAC name is 3,7-dimethylocta-1,6-dien-3-ol.

More than 200 species of plants produce linalool, mainly in the families Lamiaceae, Lauraceae and Rutaceae. It has also been found in some fungi. Linalool has been used for thousands of years as a sleep aid. Linalool is an important precursor in the formation of Vitamin E. It has a history of use in the treatment of both psychosis and anxiety, and as an anti-epileptic agent. It also provides analgesic pain relief. Its vapors have been shown to be an effective insecticide against fleas, fruit flies and cockroaches. Linalool is used as a scent in an estimated 60-80% of perfumed hygiene products and cleaning agents including soaps, detergents, shampoos and lotions. A study published in The Journal of Agriculture and Food Chemistry claims to have demonstrated that inhaling linalool can reduce stress in lab rats.

In another embodiment, the terpene/terpenoid includes myrcene. Myrcene, or -myrcene, is an olefinic natural organic compound. It is classified as a hydrocarbon, more precisely as a monoterpene. Terpenes are dimers of isoprene, and myrcene is one of the most important. It is a component of the essential oil of several plants including bay, cannabis, ylang-ylang, wild thyme, mango, parsley and hops. It is produced mainly semi-synthetically from myrcia, from which it gets its name. It is a key intermediate in the production of several fragrances. α-Myrcene is the name for the structural isomer 2-methyl-6-methylene-1,7-octadiene, which is not found in nature and is little used. Its IUPAC name is 7-methyl-3-methylene-1,6-octadiene.

Myrcene has an analgesic effect and is likely to be responsible for the medicinal properties of lemon grass tea. It has anti-inflammatory properties through Prostaglandin E2. The analgesic action can be blocked by naloxone or yohimbine in mice, which suggests mediation by alpha 2-adrenoceptor stimulated release of endogenous opioids. 3-Myrcene is reported to have anti-inflammatory properties, and is used to treat spasms, sleep disorders and pain. Myrcene appears to lower resistance across the blood to brain barrier, allowing itself and many other chemicals to cross the barrier moreeffectively.

In another embodiment, the terpene/terpenoid includes α-Pinene. α-Pinene is one of the primary monoterpenes that is physiologically critical in both plants and animals. It is an alkene and it contains a reactive four-membered ring. α-Pinene tends to react with other chemicals, forming a variety of other terpenes including D-limonene and other compounds. α-Pinene has been used for centuries as a bronchodilator in the treatment of asthma. It is highly bioavailable with 60% human pulmonary uptake with rapid metabolism. α-Pinene is an anti-inflammatory via PGE1, and appears to be a broad-spectrum antibiotic. It acts as an acetylcholinesterase inhibitor, aiding memory. Products of a-pinene which have been identified include pinonaldehyde, norpinonaldehyde, pinic acid, pinonic acid and pinalic acid.

Pinene is found in conifer, pine and orange. a-Pinene is a major constituent in turpentine. Its IUPAC name is (1S,5S)-2,6,6-Trimethylbicyclo[3.1.1]hept-2-ene ((−)-a-Pinene).

In another embodiment, the terpene/terpenoid includes β-Pinene. β-Pinene is one of the most abundant compounds released by trees. It is one of the two isomers of pinene, the other being α-pinene. It is a common monoterpene, and if oxidized in air, the allylic products of the pinocarveol and myrtenol family prevail. Its IUPAC name is 6,6-dimethyl-2-methylenebicyclo[3.1.1]heptane and is also known as 2(10)-Pinene; Nopinene; Pseudopinene. It is found in cumin, lemon, pine and other plants.

In another embodiment, the terpene/terpenoid includes caryophyllene, also known as -caryophyllene. Caryophyllene is a natural bicyclic sesquiterpene that is a constituent of many essential oils, including clove, cannabis, rosemary and hops. It is usually found as a mixture with isocaryophyllene (the cis double bond isomer) and a-humulene, a ring-opened isomer. Caryophyllene is notable for having a rare cyclobutane ring. Its IUPAC name is 4,11,11-trimethyl-8-methylene-bicyclo[7.2.0]undec-4-ene.

Caryophyllene is known to be one of the compounds that contribute to the spiciness of black pepper. In a study conducted by the Swiss Federal Institute of Technology, -caryophyllene was shown to be selective agonist of cannabinoid receptor type-2 (CB2) and to exert significant cannabimimetic, anti-inflammatory effects in mice. Anti-nociceptive, neuroprotective, anxiolytic, antidepressant and anti-alcoholic activity have been tied to caryophyllene. Because β-caryophyllene is an FDA approved food additive, it is considered the first dietary cannabinoid.

In another embodiment, the terpene/terpenoid includes citral. Citral, or 3,7-dimethyl-2,6-octadienal or lemonal, is either a pair, or a mixture of terpenoids with the molecular formula $C_{10}H_{16}O$. The two compounds are double bond isomers. The E-isomer is known as geranial or citral A. The Z-isomer is known as neral or citral B. Its IUPAC name is 3,7-dimethylocta-2,6-dienal. It is also known as citral, geranial, neral, geranialdehyde.

Citral is present in the oils of several plants, including lemon myrtle, lemongrass, verbena, lime, lemon and orange. Geranial has a pronounced lemon odor. Neral's lemon odor is not as intense, but sweet. Citral is primarily used in perfumery for its citrus quality. Citral is also used as a flavor and for fortifying lemon oil. It has strong antimicrobial qualities, and pheromonal effects in insects. Citral is used in the synthesis of vitamin A, ionone and methylionone.

In another embodiment, the terpene/terpenoid includes humulene. Humulene, also known as a-humulene or a-caryophyllene, is a naturally occurring monocyclic sesquiterpene ($C_{15}H_{24}$), which is an 11-membered ring consisting of 3 isoprene units containing three nonconjugated C=C double bonds, two of them being triply substituted and one being doubly substituted. It was first found in the essential oils of *Humulus lupulus* (hops). Humulene is an isomer of β-caryophyllene, and the two are often found together as a mixture in many aromatic plants.

Humulene has been shown to produce anti-inflammatory effects in mammals, which demonstrates potential for management of inflammatory diseases. It produces similar effects to dexamethasone, and was found to decrease the edema formation caused by histamine injections. Humulene produced inhibitory effects on tumor necrosis factor-α (TNFα) and interleukin-1β (IL-1B) generation in carrageenan-injected rats. In Chinese medicine, it is blended with β-caryophyllene and used as a remedy for inflammation.

Other exemplary terpenes/terpenoids include menthol, eucalyptol, borneol, pulegone, sabinene, terpineol, terpinolene, camphor, and thymol. In one embodiment, an exemplary terpene/terpenoid is eucalyptol.

The terpene/terpenoid can be included in the composition generally between about 0.01% and about 20% of the composition, between about 0.05% and about 10%, between about 0.1% and about 5%, between about 0.15% and about 4%, between about 0.2% and about 3%, between about 0.25% and about 2%, between about 0.3% and about 1.5%, or between about 0.4% and 1%, or about 0.5%. Alternatively each terpene/terpenoid can be included in amounts of between about 0.1% and about 3%, optionally, about 1%. Alternatively, the terpene/terpenoid amount can be about 0.01%, about 0.05%, about 0.1%, about 0.15%, about 0.2%, about 0.25%, about 0.3%, about 0.35%, about 0.4%, about 0.45%, about 0.5%, about 0.55%, about 0.6%, about 0.7%, about 0.8%, or about 1% or more. The weight percent used in the composition will also be dependent upon the weight percent of the desired cannabinoid in the cannabis preparation and will be adjusted so that the ratio of the penetration enhancer to amount of desired cannabinoid is constant.

Optionally the skin permeation enhancer includes one or more sulfoxides, such as a methylsulfoxide. Exemplary methylsulfoxides include decylmethylsulfoxide, octyl methyl sulfoxide, nonyl methyl sulfoxide, decyl methyl sulfoxide, undecyl methyl sulfoxide, dodecyl methyl sulfoxide, 2-hydroxydecyl methyl sulfoxide, 2-hydroxy-undecyl methyl sulfoxide, 2-hydroxydodecyl methyl sulfoxide and the like. In one embodiment, the sulfoxide is dodecyl methyl sulfoxide.

The amount of sulfoxide to use is generally between about 0.05% and about 4% of the composition, (w/w) between about 0.1% and about 3.5%, between about 0.15% and about 3%, between about 0.2% and about 2.5%, between about 0.3% and about 2%, between about 0.5% and about 1.5%, or between about 0.7% and 1%. Alternatively, the sulfoxide amount can be about 0.2%, about 0.4%, about 0.5%, about 0.6%, about 0.7%, about 0.8%, about 0.9%, about 1%, about 1.1%, about 1.2%, about 1.3%, about 1.4%, or about 1.5%.

The pharmaceutical compositions disclosed herein may be formulated into transdermal compositions which optionally include one or more further pharmaceutically acceptable excipients. Excipients include, by way of illustration and not limitation, solvents, thickening agents, skin penetration enhancers, wetting agents, lubricants, emollients, substances added to mask or counteract a disagreeable odor, fragrances, and substances added to improve appearance or texture of the composition. Any such excipients can be used in any dosage forms of according to the present disclosure.

Compositions of the disclosure containing excipients can be prepared by any technique known to a person of ordinary skill in the art of pharmacy, pharmaceutics, drug delivery, pharmacokinetics, medicine or other related discipline that comprises admixing an excipient with a drug or therapeutic agent.

After application of the composition to the user's skin, essentially no limitations exist as to the length of time that the composition can remain in contact with the user's skin. Since the amount of cannabis in the composition will decrease as it is absorbed into the user's skin, the composition can be removed when the amount of cannabinoid remaining in the composition decreases to an amount that is no longer effective to the user. It is to be understood that the amount of cannabinoid initially carried in the composition will affect the length of time the composition will be effective once the composition is applied to the user's skin. For example, in an exemplary embodiment of the invention, the composition contains a cannabinoid in the amount of about 10 milligrams. In such an embodiment, the composition should be removed after approximately 12 hours, and after that time replaced with a new dose of the composition for continued absorption of cannabinoid into the user's skin to provide therapeutic levels of the cannabinoid to the user. However, the composition may optionally be left on longer than, or removed sooner than, the length of time that is necessary or recommended for complete diffusion of the cannabinoid into the user's skin.

As mentioned above, the composition of the present invention placed on the skin is capable of delivering cannabis through the stratum coreum layer of the epidermis and through the dermis into the microvasculature.

Preferably, compositions of the present invention contain oneor more cannabinoids. Cannabinoids are a class of diverse chemical compounds that act on cannabinoid receptors on cells that affect neurotransmitter release in the brain. The cannabis plant produces an estimated 80+ cannabinoids, each of which has unique pharmacologic effects. $\Delta^9$-THC tetrahydrocannabinol (THC), is the primary psychoactive compound of cannabis. Cannabis refers to various strains of plants *Cannabis sativa* or *Cannabis indica*. Generally, cannabinoids are collected from the female plant.

Cannabinoids as used herein refers to any cannabinoid, also defined as any ligand of the cannabinoid receptor and related compounds. Cannabinoids include phytocannabinoids (obtained from plants) and most of these fall into the subclasses such as cannabigerol, cannabichromene, cannabidiol, cannabinol (including tetrahydrocannabinol, e.g., $\Delta^9$-THC, /$\Delta^8$-THC). Other cannabinoids include cannabicyclol, cannabielsoin, cannabinoldiol, and cannabitriol.

Exemplary cannabinoids useful for the present invention include cannabinols. In one embodiment, the invention includes tetrahydrocannabinols, including the most commonly known cannabinoid, tetrahydrocannabinol (THC). The most potent stereoisomer occurs naturally as $\Delta^9$-THC where the two chiral centers at C-6a and C-10a are in the trans configuration as the (−)-trans-isomer, and this stereoisomer is also known as dronobinol. There are seven double bond isomers in the partially saturated carbocylic ring including $\Delta^{6,7}$ tetrahydrocannabinol, $\Delta^7$-tetrahydrocannabinol, $\Delta^8$-tetrahydrocannabinol, $\Delta^{9,11}$ tetrahydrocannabinol, $\Delta^{10}$ tetrahydrocannabinol, $\Delta^9$-tetrahydrocannabinol, and $\Delta^{6a,10a}$-tetrahydrocannabinol, using the dibenzopyran numbering:

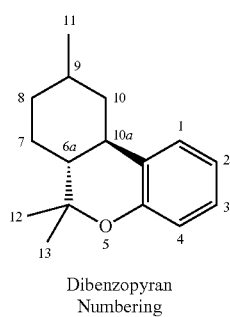 [SMILES: CC1CC[C@@H]2[C@@H](C1)c1ccccc1OC2(C)C]

Dibenzopyran Numbering

The cannabinols have the following general structure:

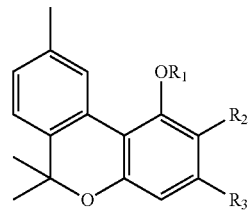

$R_1$ = H or $C_2$
$R_2$ = H or COOH
$R_3$ = $C_1$, $C_3$, $C_4$, or $C_5$ side chain
Cannabinol type Below is $\Delta^9$-tetrahydrocannabinol.

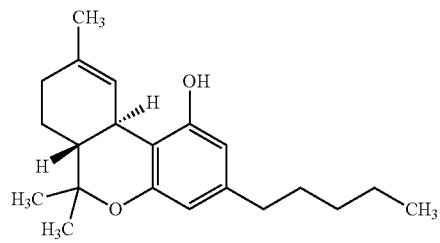 [SMILES: CCCCCc1cc(O)c2c(c1)OC(C)(C)[C@@H]1CCC(C)=C[C@@H]21]

Tetrahydrocannabinol, such as $\Delta^9$ THC, helps reduce nausea and vomiting, which is particularly helpful to patients undergoing chemotherapy for cancer. Patients suffering from AIDS often experience a lack of appetite, of which tetrahydrocannabinol is also helpful in counteracting. Tetrahydrocannabinol is also useful for glaucoma relief.

THC may be derived from *Cannabis sativa* or *Cannabis indica*, for example.

A cannabinol useful for the present invention also includes tetrahydrocannabivarin (THCv) having a propyl side chain.

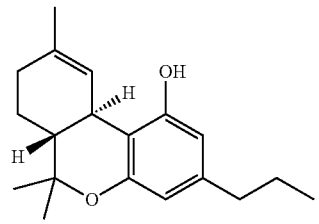 [SMILES: CCCc1cc(O)c2c(c1)OC(C)(C)[C@@H]1CCC(C)=C[C@@H]21]

Tetrahydrocannabivarin—THCV is structurally similar to THC, but acts an antagonist to the CB1 & CB2 receptors in the body. Given this, recent studies have shown that THCV is an excellent appetite suppressant as it blocks the rewarding sensations experienced when eating. THCV also holds anti-convulsive properties useful for treating epilepsy. While psychoactive, THCV lends itself to a shorter, psychedelic, clear-headed effect which is shorter lasting that THC.

A cannabinoid useful for the present invention also includes cannabinol (CBN).

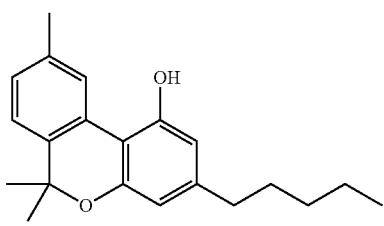 [SMILES: CCCCCc1cc(O)c2c(c1)OC(C)(C)c1ccc(C)cc1-2]

CBN's primary effects are as an anti-epileptic, antispasmodic and reliever of intra-ocular pressure. Recent studies suggest that CBN can be administered as an antidepressant, can be used to prevent convulsions and to sedate patients experiencing pain. It is ideal for those suffering from glaucoma, inflammation, and insomnia.

A cannabinoid useful for the present invention also includes a cannabidiol type.

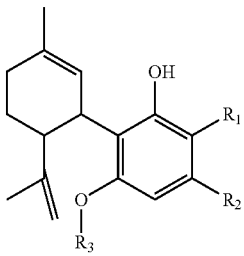

$R_1$ = H or COOH
$R_2$ = $C_1$, $C_3$, $C_4$ or $C_5$ side chain
$R_3$ = H or $CH_3$ A cannabinoid useful for the present invention also includes the naturally occurring cannabidiol type also called (−)-trans-cannabidiol (CBD).

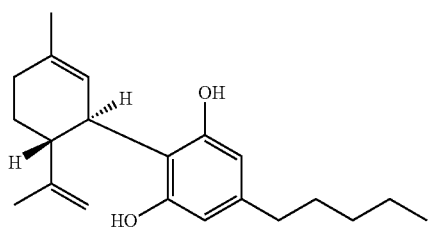 [SMILES: C=C(C)[C@@H]1CCC(C)=C[C@H]1c1c(O)cc(CCCCC)cc1O]

CBD can occur in up to 40% of the cannabinoid extracts from cannabis. CBD generally occurs in the cannabis plant prior to processing as CBDa which has a carboxylic acid at $R^1$. The 2-carboxylic acids of the cannabinoids can be decarboxylated by heat, light, or alkaline conditions to their respective decarboxylated compounds.

CBD and CBDa have been shown effective in treating inflammation, diabetes, cancer, mood disorders (PTSD to ADD) and neurodegenerative diseases such as Alzheimer's. It has been shown to have anti-convulsive, anti-anxiety, anti-psychotic, anti-nausea and anti-rheumatoid arthritic and sedative properties, and a clinical trial showed that it eliminates anxiety and other unpleasant psychological side effects. CBD does not display the psychoactive effects of $11^9$-THC. CBD was found in one study to be more effective than aspirin for pain relief and reducing inflammation. CBD has been shown to be a potent antioxidant as well as having neuroprotective and anti-inflammatory uses.

A cannabinoid useful for the present invention also includes cannabichromene type or

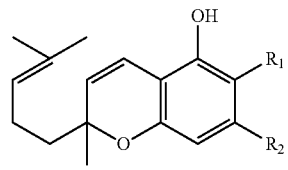

$R_1$ = H or COOH
$R_2$ = $C_3$ or $C_5$ side chain
Cannabichromene type

An exemplary cannabichromene (CBC) is shown below:

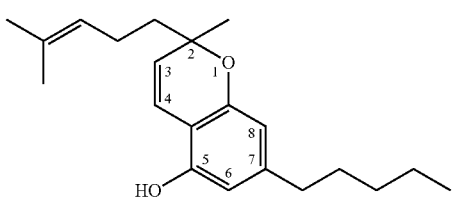 [SMILES: CCCCCc1cc(O)c2c(c1)OC(C)(CCC=C(C)C)C=C2]

CBC, like THC and CBD, results from CBCa. CBC has been shown to inhibit the growth of cancerous tumors due to its interaction with anadamide, a human endocannabinoid. It is also an inflammation and pain inhibitor and has been successful for treating migraines and stimulating bone growth. Due to its small quantity in the cannabis plant, CBC works best in conjunction with CBD and THC.

The cannabinoids include cannabinoids which have a carboxylic acid substituent, also known as cannabinoid acids, such as tetrahydrocannabinolic acid (THCa) which has a carboxylic acid at $R^2$. These carboxylic acids are designated as "a". For example, CBD occurs as CBDa in the cannabis plant. The 2-carboxylic acids of the cannabinoids can be decarboxylated by heat, light, or alkaline conditions to their respective decarboxylated compounds, such as to $\Delta^9$-THC. See below for the structure of $\Delta^9$-THCa.

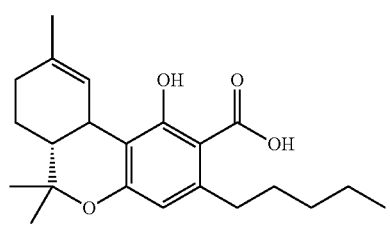

Decarboxylation of the cannabinoid acids to the corresponding phenols occurs over time, upon heating, or under alkaline conditions. Heating for 5 minutes at a temperature of 200-210° C. will accomplish decarboxylation. THCa is the non-activated, non-psychotropic acid form of THC. THCa is a known anti-inflammatory and provides many of the same benefits of THC but without psychotropic side effects. THCa not only has anti-proliferative abilities that are crucial in helping inhibit the growth of cancerous cells, but also, it has anti-spasmodic abilities that helps subdue muscle spasms and therefore has potential use among epileptic patients.

Cannabinoids may also be administered as their pharmaceutically acceptable salts.

Cannabinoids to use in the present invention include any of the cannabinoids as discussed above. In one embodiment, the cannabinoid to use is CBN, CBDa, CBD, THC, THCa, or mixtures of CBD (or CBDa) and THC (or THCa). Mixtures of CBD or CBDa and THC or THCa can be, for example, 1:1 w/w or any other mixture. Various ratios of the above-described cannabinoids can be used for the transdermal applications described herein. The ratios can be adjusted based on pharmacological effects required. For example, particular cannabinoids can be enriched and/or purified from a cannabis extract via techniques such as fractional distillation or adjusting the harvesting technique of the plants. Ratios of enriched/purified cannabinoids for the cannabinoid products of the invention can be adjusted, such as, for example, 1:1 w/w CBD:THC. Ratios include 0.1:1, 0.2:1, 0.3:1, 0.4:1, 0.5:1, 0.6:1, 0.7:1, 0.8:1, 0.9:1, 1:1, 1:1.2, 1:1.5, 1:1.3, 1:1.5, 1:1.7, 1:2, 1:3, 1:4, 1:5, 1:6, 1:7, 1:8 or 1:10 (all ratios given are w/w).

In order to deliver the desired cannabinoids, in one embodiment, the selection of an appropriate strain of cannabis which is enriched in the desired cannabinoid can be utilized. For example, a strain of cannabis can be selected that is CBDa, or dominant in THCa. In another embodiment, separation and/or extraction methods as known in the art can be used to enrich in the desired cannabinoid. Processing methods may also be utilized to enrich in the desired cannabinoid; for example, CBN can be produced upon longer exposure to heat.

Cannabinoids to use in the present invention also include the carboxylic acid forms of cannabinoids, or the cannabinoid acids. Without being bound by theory, the inventors use processes to obtain preparations of THCa and CBDa, for example, which do not decarboxylate the naturally occurring cannabinoid acids such as THCa and CBDa. When the cannabinoid acids are desired for use, the present invention avoids the use of steps such as heat and/or drying which can result in decarboxylation of the alkaloids (i.e., carboxylic acid forms) to minimize or prevent decarboxylation.

In some embodiments individual doses of the compositions of the present invention contain from about 0.1 to about 100 milligrams (mg) of cannabinoid, from about 0.5 to about 50 mg, from about 1 to about 40 mg, from about 2 to about 20 mg, from about 5 mg to about 15 mg, or about 0.1 mg, 0.5 mg, 1 mg, 2 mg, 3 mg, 4 mg, 5 mg, 6 mg, 8 mg, 10 mg, 12 mg, 14 mg, 16 mg, 18 mg, 20 mg, 30 mg, 40 mg, 50 mg, 60 mg, 80 mg or more per dose.

The composition may be standardized to contain the desired amount of the particular cannabinoid desired. For example, out of a cannabinoid preparation, the amount of cannabinoid of interest is quantitated by laboratory test and the amount of cannabinoid preparation to add to the composition is determined by the amount to add to result in the desired amount of the particular cannabinoid. For example, if a cannabis preparation contains 50% by weight of the desired cannabinoid, the remaining ingredients are adjusted to correspond to the amount of the desired cannabinoid.

The cannabinoid amount, in terms of weight percent, in the composition is generally between about 0.01% and about 5% of the composition, between about 0.05% and about 4%, between about 0.1% and about 3.5%, between about 0.2% and about 3%, between about 0.4% and about 2%, or between about 0.6% and about 1.5%. In one embodiment, the amount is between about 0.8% and 1.2%, or about 1%. Alternatively, the cannabinoid amount can be about 0.01%, about 0.05%, about 0.1%, about 0.2%, about 0.4%, about 0.6%, about 0.8%, about 0.9%, about 1%, about 1.1%, about 1.2%, about 1.4%, about 1.6%, about 1.8%, about 2%, about 3%, about 4%, about 5%, about 6%, about 8%, about 10%, about 15%, or about 20%. The remaining ingredients are adjusted to maintain the desired weight percent of the desired cannabinoid. As discussed above, in one embodiment, the composition provides an individual dose of about 10 mg of cannabinoid.

The cannabis preparation may be prepared by any method known in the art. In one embodiment, cannabis plant matter is extracted with a solvent such as heptane, butane, hexane, isopropyl alcohol, ethanol, and liquid, dry ice or supercritical $CO_2$. Extraction conditions can vary depending on whether the cannabinoid acids ("a forms") are desired or the decarboxylated cannabinoids are desired. Cold extraction methods can be used when the acids are desired. The solvent may then be removed from the extract by any method known in the art, including vacuum and/or distillation/evaporation. The resultant extract (cannabis preparation) is normally in an oil form or viscous oil form. Cannabis oil which has not been heated generally comprise the cannabinoid acids or "a" forms comprising the carboxylic acid substituent as discussed elsewhere herein.

To improve the rate at which the cannabis diffuses through the stratum corneum layer of the epidermis, optional excipients are included in the polymer matrix. The excipients can consist of a carrier agent, a permeation enhancer, an adhesive, and/or a terpene. Some compounds named can act simultaneously as carrier agents and permeation enhancers, or have other functions such as pharmaceutical activity, but for convenience are described as either one or the other herein.

The transdermal delivery involves contacting the composition comprising one or more cannabinoids with the subject's skin under conditions effective for at least one of the provided cannabinoids to penetrate the skin and enter the bloodstream. The compositions of the present invention allow for significant transdermal delivery across the skin. A number of methods known in the art can be used to assess delivery across the skin. In one method, delivery may be assessed by measurement of the remaining cannabinoid in the composition after use. After the composition was present on the skin of a patient for at least 12 hours, for example, at least 0.1% of the cannabinoid can be delivered across the skin, at least 0.5% of the cannabinoid can be delivered across the skin, at least 1% of the cannabinoid can be delivered across the skin, at least 2% of the cannabinoid can be delivered across the skin, at least 3% of the cannabinoid can be delivered across the skin, at least 4% of the cannabinoid can be delivered across the skin, at least 5% of the cannabinoid can be delivered across the skin, at least 6% of the cannabinoid can be delivered across the skin, at least 7% of the cannabinoid can be delivered across the skin, at least 8% of the cannabinoid can be delivered across the skin, at least 9% of the cannabinoid can be delivered across the skin, at least 10% of the cannabinoid can be delivered across the skin, at least 11% of the cannabinoid can be delivered across the skin, at least 12% of the cannabinoid can be delivered across the skin, at least 14% of the cannabinoid can be delivered across the skin, at least 16% of the cannabinoid can be delivered across the skin, at least 18% of the cannabinoid can be delivered across the skin, at least 20% of the cannabinoid can be delivered across the skin, at least 25% of the cannabinoid can be delivered across the skin, at least 30% of the cannabinoid can be delivered across the skin, at least 35% of the cannabinoid can be delivered across the skin, at least 40% of the cannabinoid can be delivered across the skin, at least 45% of the cannabinoid can be delivered across the skin, at least 50% of the cannabinoid can be delivered across the skin, at least 55% of the cannabinoid can be delivered across the skin, at least 60% of the cannabinoid can be delivered across the skin, at least 65% of the cannabinoid can be delivered across the skin, at least 70% of the cannabinoid can be delivered across the skin, at least 75% of the cannabinoid can be delivered across the skin, at least 80% of the cannabinoid can be delivered across the skin, at least 85% of the cannabinoid can be delivered across the skin, at least 90% of the cannabinoid can be delivered across the skin, or at least 95% of the cannabinoid can be delivered across the skin, as measured by residual drug after the intended use period.

In one embodiment, compositions described herein are suitable for transdermal administration. In another embodiment, transdermally administrable compositions are adapted for administration in and/or around the abdomen, back, chest, legs, arms, scalp or other suitable skin surface and may include formulations in which the cannabinoid(s) are administered in patches, ointments, creams, suspensions, lotions, pastes, gels, sprays, foams or oils.

Therefore, disclosed are transdermal methods of delivery whereby cannabinoids can be delivered and be made systemically available to a mammal in a therapeutically effective amount. In addition to the benefits of systemically administered cannabinoids, there are also localized benefits from topical administration. For example, topically administered cannabinoids are useful to alleviate pain and other conditions originating near the surface of the skin.

Also disclosed in the present invention are methods for the transdermal delivery of a cannabinoid to a user, the method comprising application of a composition according to the instant invention to the skin of a human whereby one or more cannabinoids are delivered to the human. Cannabinoids of the instant invention are useful to provide effects on the human including analgesic, anti-inflammatory, sedative, anti-cancer, neuroprotective and anti-oxidant effects. Cannabinoids can be used for treatment of conditions such as oxidation associated diseases, including ischemic, age-related, inflammatory and autoimmune diseases, as well as limiting neurological damage following ischemic insults, such as stroke and trauma, or in the treatment of neurodegenerative diseases, such as Alzheimer's disease, Parkinson's disease and HIV dementia. In one embodiment, delivery of a cannabinoid via the compositions of the present invention can be used to treat pain, nausea and emesis, convulsions, muscle spasm, inflammation, depression, and cachexia.

It is known in the art that specific cannabinoid receptors exist in the brain and other organs and recognize cannabinoids and trigger cell responses. CB1 receptors are found in high concentrations within the central nervous system and are also present in peripheral tissues such as neurons, endocrine glands, leukocytes, spleen, heart and parts of the reproductive, urinary and gastrointestinal tracts. CB2 receptors are expressed primarily by immune cells and tissues, such as leukocytes, spleen and tonsils. Endogenous cannabinoids which are produced by the human body include anandamide (arachidonyl-ethanolamide, 2-arachidonyl glycerol, and palmitylethanolamide).

Clinical studies of the effects of cannabinoids on chronic pain showed that THC had analgesic effects similar to codeine, as well as anti-emesis and enhanced appetite. See Noyes et al., *Clinical Pharmacology and Therapeutics* 15 (1975): 139-145. Other research showed that cannabis and cannabinoids also work as anti-inflammatories. It is speculated that cannabinoids act on CB2 receptors located on mast cells and attenuate the release of inflammatory agents. There have also been research studies to show that cannabis' other components, such as flavonoids and terpenoids, may act in synergy to contribute to anti-inflammatory effects.

While various aspects and features of certain embodiments have been summarized above, the following detailed description illustrates a few embodiments in further detail to enable one of skill in the art to practice such embodiments. The described examples are provided for illustrative purposes and are not intended to limit the scope of the invention.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

EXAMPLES

The following examples are provided for illustrative purposes only and are not intended to limit the scope of the invention.

Example 1

Preparation of transdermal composition. The cannabis essential oil containing cannabinoids was extracted from cannabis by solvent extraction (either heptane, supercritical carbon dioxide, or ethanol). The oil was purified under vacuum pressure and heat. The obtained cannabis preparation was then tested to quantititate the levels of cannabinoid THC.

PLO gel was obtained from Apothecares (Decatur, Ala.), called Apothederm base, made up of PLO gel is obtained from Apothecares (Decatur, Ala.), and includes water, PPG-2 myristyl ether propionate, soy lecithin, ethyl alcohol, PEMULEN TR1, aminomethyl propanol, potassium sorbate, methylparaben, CARBOPOL 2020, propylparaben, and bronopol.

To prepare a transdermal composition, 0.1 g of extract (100% THC) is combined with 0.05 g menthol, 0.1 g isopropyl myristate, 0.05 g scent, and 9.5 g PLO gel, resulting in about 9.8 g composition. 10 mg was administered (about 1 g) per patient per dose.

To prepare another transdermal composition, 0.06 g of extract (60% THC) is combined with 0.03 g menthol, 0.06 g isopropyl myristate, 0.03 g scent, and 5.7 g PLO gel, resulting in about 5.88 g composition. 10 mg was administered (about 1 g) per patient per dose.

To prepare another transdermal composition, 0.05 g of extract (50% THC) is combined with 0.025 g menthol, 0.05 g isopropyl myristate, 0.025 g scent, and 4.75 g PLO gel. 10 mg was administered (about 1 g) per patient per dose.

To prepare a transdermal composition, 0.1 g of extract (100% THC-a) is combined with 0.05 g menthol, 0.1 g isopropyl myristate, 0.05 g scent, and 9.5 g PLO gel, resulting in about 9.8 g composition. 10 mg was administered (about 1 g) per patient per dose.

To prepare another transdermal composition, 0.06 g of extract (60% THC-a) is combined with 0.03 g menthol, 0.06 g isopropyl myristate, 0.03 g scent, and 5.7 g PLO gel, resulting in about 5.88 g composition. 10 mg was administered (about 1 g) per patient per dose.

To prepare another transdermal composition, 0.05 g of extract (50% THC-a) is combined with 0.025 g menthol, 0.05 g isopropyl myristate, 0.025 g scent, and 4.75 g PLO gel. 10 mg was administered (about 1 g) per patient per dose.

To prepare a transdermal composition, 0.1 g of extract (100% CBD) is combined with 0.05 g menthol, 0.1 g isopropyl myristate, 0.05 g scent, and 9.5 g PLO gel, resulting in about 9.8 g composition. 10 mg was administered (about 1 g) per patient perdose.

To prepare another transdermal composition, 0.06 g of extract (60% CBD) is combined with 0.03 g menthol, 0.06 g isopropyl myristate, 0.03 g scent, and 5.7 g PLO gel, resulting in about 5.88 g composition. 10 mg was administered (about 1 g) per patient per dose.

To prepare another transdermal composition, 0.05 g of extract (50% CBD) is combined with 0.025 g menthol, 0.05 g isopropyl myristate, 0.025 g scent, and 4.75 g PLO gel. 10 mg was administered (about 1 g) per patient per dose.

To prepare a transdermal composition, 0.1 g of extract (100% CBN) is combined with 0.05 g menthol, 0.1 g isopropyl myristate, 0.05 g scent, and 9.5 g PLO gel, resulting in about 9.8 g composition. 10 mg was administered (about 1 g) per patient perdose.

To prepare another transdermal composition, 0.06 g of extract (60% CBN) is combined with 0.03 g menthol, 0.06 g isopropyl myristate, 0.03 g scent, and 5.7 g PLO gel, resulting in about 5.88 g composition. 10 mg was administered (about 1 g) per patient per dose.

To prepare another transdermal composition, 0.05 g of extract (50% CBN) is combined with 0.025 g menthol, 0.05 g isopropyl myristate, 0.025 g scent, and 4.75 g PLO gel. 10 mg was administered (about 1 g) per patient per dose.

To prepare a transdermal composition, 0.1 g of extract (100% of a THC:CBD 1:1 mixture) is combined with 0.05 g menthol, 0.1 g isopropyl myristate, 0.05 g scent, and 9.5 g PLO gel, resulting in about 9.8 g composition. 10 mg was administered (about 1 g) per patient per dose.

To prepare another transdermal composition, 0.06 g of extract (60% of a THC:CBD 1:1 mixture) is combined with 0.03 g menthol, 0.06 g isopropyl myristate, 0.03 g scent, and 5.7 g PLO gel, resulting in about 5.88 g composition. 10 mg was administered (about 1 g) per patient per dose.

To prepare another transdermal composition, 0.05 g of extract (50% of a THC:CBD 1:1 mixture) is combined with 0.025 g menthol, 0.05 g isopropyl myristate, 0.025 g scent, and 4.75 g PLO gel. 10 mg was administered (about 1 g) per patient per dose.

To prepare a transdermal composition, 0.1 g of extract (100% CBDa) is combined with 0.05 g menthol, 0.1 g isopropyl myristate, 0.05 g scent, and 9.5 g PLO gel, resulting in about 9.8 g composition. 10 mg was administered (about 1 g) per patient per dose.

To prepare another transdermal composition, 0.06 g of extract (60% CBDa) is combined with 0.03 g menthol, 0.06 g isopropyl myristate, 0.03 g scent, and 5.7 g PLO gel, resulting in about 5.88 g composition. 10 mg was administered (about 1 g) per patient per dose.

To prepare another transdermal composition, 0.05 g of extract (50% CBDa) is combined with 0.025 g menthol, 0.05 g isopropyl myristate, 0.025 g scent, and 4.75 g PLO gel. 10 mg was administered (about 1 g) per patient per dose.

Use. In the research and development of the cannabidiol (CBD) transdermal gel pen, a study was conducted with human volunteers suffering from broad-spectrum pain.

An amount of 2 mg CBD was applied to the inner wrist of 10 volunteers each reporting pain levels of 4-9 on the pain management scale of 1-10. The application site was cleaned with isopropyl alcohol before application. The area was washed with soap and water after wear.

After 10 minutes, 5 volunteers reported a reduction of 2 points or more on the pain management scale. After 20 minutes, 8 volunteers reported that their pain was reduced 2 points or more from their initial pain level. Thirty minutes after initial application of the gel, 9 of the 10 volunteers reported a reduction of at least 50% of their initial pain level. Six volunteers reported pain levels of O or I on the pain management scale at the 30-minute mark.

Nine of the 10 volunteers experienced therapeutic effects of pain relief, which had a duration ranging from 4-12 hours. 80% of the volunteers reported the level of relief attained within the first 30 minutes remained consistent for 2 hours or more. 40% of the volunteers reported a consistent level of pain relief for 4 hours or more. 20% of volunteers reported a consistent level of pain relief for 6 hours or more after initial application. One volunteer reported that pain was relieved for more than 12 hours.

Wear testing. The transdermal gel compositions were tested by determining how much of the cannabinoid remained on the surface of the skin I0, 20, 30, and 60 minutes after application by the same 10 human volunteers. It was found that after 20 minutes, no measurable quantity of the cannabinoids remained on the skin, indicating complete diffusion into the skin of all 10 volunteers within 20 minutes.

Example 2

THCa Transdermal Patch for Arthritis Pain & Inflammation. In the research and development of the THCa transdermal patch, a study was conducted with human volunteers suffering from inflammation and pain related to arthritis. The patches were prepared in the manner disclosed in applications U.S. 61/981,640 and U.S. 62/087,390, which are incorporated herein by reference in their entirety.

Use. One-10 mg THCa patch was applied to the inner wrist of 10 volunteers reporting moderate to severe pain and inflammation related to arthritis. The application site was cleaned with isopropyl alcohol before application. The area was washed with soap and water after wear.

Immediately prior to application, volunteers were asked to rate their pain level on the standard 1-10 pain management scale. Volunteers reported pain ratings ranging from 3 to 7.

After 10 minutes, 2 volunteers reported a reduction of 2 points or more on the pain management scale. After 20 minutes, 4 volunteers reported that their pain was reduced 2 points or more from the initial pain level they reported. Thirty minutes after initial application of the patch, 7 of the 10 volunteers reported that their pain was reduced 2 points or more. Five of the volunteers reported complete, or near complete, relief of both inflammation and pain, with ratings of 0 to 1.

Seven of the 10 volunteers experienced therapeutic effects of pain and inflammation relief, which had a duration ranging from 6-12 hours. 80% of the volunteers that reported any level of relief reported that the level of relief attained within the first 30 minutes remained consistent for 4 hours or more. 50% of the volunteers reported a consistent level of pain relief for 8 hours or more. 20% of volunteers reported a consistent level of pain relief for 10 hours or more after initial application.

THC-Sativa Transdermal Patch Testing Vs Placebo

In the research and development of the THC-Sativa transdermal patch, a study was conducted with human volunteers. The group of 20 volunteers was randomly divided into 2 groups of 10.

Use. One-20 mg THC-Sativa patch was applied to the inner wrist of 10 of the volunteers (Group A). The other group of 10 volunteers was administered a patch with no active ingredient (Group B). The application site was cleaned with isopropyl alcohol before application. The area was washed with soap and water after wear.

Group A

Ten minutes after initial application of the THC-Sativa patch, 2 volunteers reported mild energetic effects. Twenty minutes after application of the patch, 5 volunteers reported energetic effects. Thirty minutes after application, 8 of the 10 volunteers reported energetic effects. Two volunteers did not report noticeable effects.

Eight of the 10 volunteers experienced noticeable effects, which had a duration ranging from 4-12 hours. Of the volunteers that reported effects, 80% reported the effects attained within the first 30 minutes remained consistent for 4 hours or more. 60% of the volunteers reported that effects remained consistent for 6 hours or more. 20% of volunteers reported effects lasting for 8 hours or more after initial application. 10% of volunteers reported effects lasting 12 hours after initial application.

Group B

After 10 minutes, 0 volunteers reported feeling any effects or changes. After 20 minutes, one volunteer reported mild feelings of energy and light-headedness. Thirty and 60 minutes after initial application of the patch, 0 volunteers in Group B reported noticeable effects.

CBN Transdermal Patch for Insomnia

In the research and development of the Cannabinol (CBN) transdermal patch, a study was conducted with human volunteers suffering from insomnia and related sleep disorders.

Use. One-10 mg CBN patch was applied to the inner wrist of 10 volunteers reporting insomnia and/or ongoing difficulty sleeping. The application site was cleaned with isopropyl alcohol before application. The area was washed with soap and water after wear.

Volunteers were asked to rate their average quality of sleep for 7 nights prior to the use of the CBN patch, and then report any change in quality of sleep the night that a CBN patch had been administered. Nine out of the 10 volunteers reported at least a 25% improvement in sleep quality and reduction in time to fall asleep. Seven out of 10 volunteers reported a 75% or greater improvement in sleep quality and reduction in time to fall asleep. Nine of the 10 volunteers reported effects that supported restful sleep of 8 to12 hours the night when the CBN patch was administered.

Transdermal Patch Wear Testing

In the research and development of the transdermal patch, a study was conducted with human volunteers to determine the lasting effects of the patch.

Use. Five-10mg transdermal patches were applied to the inner arm of 5 volunteers. After each 3-hour interval following application of the patches, one patch was removed from each volunteer and tested for remaining active cannabinoids. The application site was cleaned with isopropyl alcohol before application. The area was washed with soap and water after wear.

Three hours after initial application, the first patch was removed from all 5 volunteers. The patches contained a range of 60-75% of the original 10 mg of cannabinoids, with an average of 66% of cannabinoids remaining amongst the 5 patches tested.

Six hours after initial application, a second patch was removed from all 5 volunteers. The patches removed contained a range of 35-50% of the original 10 mg of cannabinoids, with an average of 44% of cannabinoids remaining amongst the 5 patches tested.

Nine hours after initial application, a third patch was removed from all 5 volunteers. The patches removed contained a range of 10-30% of the original 10 mg of cannabinoids, with an average of 17% of cannabinoids remaining amongst the 5 patches tested.

Twelve hours after initial application, a fourth patch was removed from all 5 volunteers. The patches removed contained a range of 0-2% of the original 10 mg of cannabinoids, with an average of less than 1% of cannabinoids remaining amongst the 5 patches tested.

Fifteen hours after initial application, the fifth patch was removed from all 5 volunteers. No measurable cannabinoids remained on any of the 5 patches that were tested, indicating complete absorption for all volunteers in less than 15 hours.

The variances noted among time to absorption for volunteers is likely attributable to body composition and metabolism.

Example 3

A transdermal formulation was made with the following ingredients: water, 10% w/w; lecithin, 15% w/w; PPG-myristyl ether propionate, 2%; acrylate crosspolymers (CARBOPOL), 2%; aminomethyl propanol, 2%; ethyl alcohol, 5%; methyl paraben, 1%; propyl paraben, 1%; bronopol, 1%; potassium sorbate, 1%; tocopherol, 1%; camphor, 1%; myrcene, 1%; limonene, 1%; terpinolene, 1%; beta carophyllene, 1%; glycerin, 5%; isopropyl myristate, 32%; cannabis oil, 2%; polysorbate, 2%; and oleic acid 13%.

The amount of water in the above formulation was varied from 10%, 20%, and 30%. Isopropyl myristate was varied in each formulation to be 32%, 28%, and 23%, respectively and oleic acid was varied in each formulation to be 13%, 8%, and 3%, respectively. FIG. 1 shows the results. All formulations show acceptable delivery across a skin cell model (Franz diffusion cell), with 10% water showing the highest delivery.

The description of the various embodiments has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiments described and shown in the FIGURES were chosen and described in order to explain the principles of the invention, the practical application, and to enable others of ordinary skill in the art to understand the invention for various embodiments with various modifications as are suited to the particular use contemplated. All references cited herein are incorporated in their entirety by reference.

What is claimed is:

1. A transdermal composition comprising a pharmaceutically effective amount of a cannabinoid for delivery of the cannabinoid to the bloodstream of a user, said composition comprising:

a) a surfactant-lecithin organogel comprising a mixture of: water, high molecular weight acrylic acid polymers, PPG-2 myristyl ether propionate, at least one exogenous terpene or terpenoid, and oleic acid; and
b) at least one cannabinoid;
   wherein the cannabinoid is capable of diffusing from the composition into the bloodstream of the user.

2. The composition of claim 1, wherein the surfactant-lecithin organogel is present in an amount of between about between about 95% and about 98% w/w.

3. The composition of claim 1, wherein the terpene or terpenoid comprises myrcene or menthol.

4. The composition of claim 1, wherein the composition further comprises isopropyl myristate.

5. The composition of claim 1, wherein the cannabinoid comprises THC.

6. The composition of claim 5, wherein the THC is in an amount between about 0.1% and about 3%.

7. The composition of claim 1, wherein the cannabinoid comprises THCa.

8. The composition of claim 7, wherein the THCa is in an amount between about 0.1% and about 3%.

9. The composition of claim 1, wherein the cannabinoid comprises CBD.

10. The composition of claim 9, wherein the CBD is in an amount between about 0.1% and about 3%.

11. The composition of claim 1, wherein the cannabinoid comprises CBDa.

12. The composition of claim 11, wherein the CBDa is in an amount between 0.1% and about 3%.

13. The composition of claim 1, wherein the cannabinoid comprises CBN in an amount of between 0.1% and about 3%.

14. The composition of claim 1, wherein the cannabinoid comprises CBC in an amount of 0.1% and about 3%.

15. The composition of claim 1, wherein the cannabinoid comprises THCv in an amount of between about 0.1% and about 3%.

16. The composition of claim 1, wherein the cannabinoid comprises CBC in an amount of between about 0.1% and about 3%.

17. A method for treating a patient suffering from a condition selected from the group consisting of pain, nausea and emesis, convulsions, muscle spasm, inflammation, depression, and cachexia comprising administering the composition of claim 1.

18. The composition of claim 1, wherein water is present in an amount between about 1% to 30%.

19. The composition of claim 1, wherein water is present in an amount between about 4% to 20%.

20. The composition of claim 1, wherein water is present in an amount between about 8% to 12%.

* * * * *